(12) United States Patent
Lombardo

(10) Patent No.: US 11,490,884 B2
(45) Date of Patent: Nov. 8, 2022

(54) KNOTLESS SUTURE ANCHOR AND DEPLOYMENT DEVICE

(71) Applicant: ConMed Corporation, Utica, NY (US)

(72) Inventor: Giuseppe Lombardo, Trinity, FL (US)

(73) Assignee: ConMed Corporation, Utica, NY (US)

(*) Notice: Subject to any disclaimer, the term of this patent is extended or adjusted under 35 U.S.C. 154(b) by 378 days.

(21) Appl. No.: 15/381,313

(22) Filed: Dec. 16, 2016

(65) Prior Publication Data

US 2017/0172562 A1 Jun. 22, 2017

Related U.S. Application Data

(60) Provisional application No. 62/268,028, filed on Dec. 16, 2015.

(51) Int. Cl.
*A61B 17/04* (2006.01)

(52) U.S. Cl.
CPC .... *A61B 17/0401* (2013.01); *A61B 2017/044* (2013.01); *A61B 2017/0409* (2013.01); *A61B 2017/0414* (2013.01); *A61B 2017/0445* (2013.01); *A61B 2017/0458* (2013.01); *A61B 2017/0464* (2013.01)

(58) Field of Classification Search
CPC ........ A61B 17/0401; A61B 2017/0409; A61B 2017/0414; A61B 2017/044; A61B 2017/0445; A61B 2017/0448; A61B 2017/0464
See application file for complete search history.

(56) References Cited

U.S. PATENT DOCUMENTS

| | | | | |
|---|---|---|---|---|
| 4,175,555 A | * | 11/1979 | Herbert | A61B 17/863 606/304 |
| 5,019,079 A | * | 5/1991 | Ross | A61B 17/863 411/389 |

(Continued)

FOREIGN PATENT DOCUMENTS

JP 2000230528 8/2000

OTHER PUBLICATIONS

International Search Report Form PCT/ISA/210 and Written Opinion of the International Searching Authority Form PCT/ISA/237; dated Jul. 28, 2017 (Jul. 28, 2017); 18 pages, PCT/US2016/067114.

(Continued)

*Primary Examiner* — Tuan V Nguyen
(74) *Attorney, Agent, or Firm* — Bond, Schoeneck & King, PLLC; Frederick J. M. Price

(57) ABSTRACT

A deployment device, including a driver shaft; an implant attached to the distal end of the driver shaft; a handle assembly connected to the proximal end of the driver shaft including a handle and a knob positioned distally to the handle; a cleat configured to secure a proximal end of a suture received from the implant through an aperture of the driver shaft resulting in a first applied tension value when the implant is placed in a pilot hole, wherein each of the implant, proximal handle and cleat is connected to the driver shaft such that rotation of the proximal handle in a first direction results in the rotation of the implant in the first direction and the maintenance of at least 50% of the first applied tension value when the implant is rotated in the first direction and advanced in the distal direction within the pilot hole.

19 Claims, 13 Drawing Sheets

(56) References Cited

U.S. PATENT DOCUMENTS

| | | | |
|---|---|---|---|
| 5,908,426 A * | 6/1999 | Pierce | A61B 17/062 606/139 |
| 5,997,541 A * | 12/1999 | Schenk | A61B 17/68 606/303 |
| 6,030,162 A * | 2/2000 | Huebner | A61B 17/1682 411/263 |
| 6,544,281 B2 * | 4/2003 | ElAttrache | A61B 17/0401 606/232 |
| 7,329,272 B2 | 2/2008 | Burkhart et al. | |
| 7,582,107 B2 * | 9/2009 | Trail | A61B 17/8635 606/304 |
| 7,867,252 B2 * | 1/2011 | Criscuolo | A61B 17/864 606/232 |
| 7,993,369 B2 | 8/2011 | Dreyfuss | |
| 8,298,262 B2 | 10/2012 | Stone et al. | |
| 8,430,909 B2 | 4/2013 | Dreyfuss et al. | |
| 8,435,264 B2 * | 5/2013 | Sojka | A61B 17/0401 606/232 |
| 8,460,340 B2 | 6/2013 | Sojka et al. | |
| 8,663,279 B2 | 3/2014 | Burkhart et al. | |
| 8,758,367 B2 * | 6/2014 | Philippon | A61B 17/0401 606/139 |
| 8,845,685 B2 | 9/2014 | Stone et al. | |
| 8,939,983 B2 | 1/2015 | Stone et al. | |
| 9,005,246 B2 | 4/2015 | Burkhart et al. | |
| 9,101,355 B2 * | 8/2015 | Lantz | A61B 17/0401 |
| 9,179,907 B2 | 11/2015 | Elattrache et al. | |
| 9,265,496 B2 | 2/2016 | Sojka et al. | |
| 9,277,910 B2 * | 3/2016 | Nason | A61B 17/0401 |
| 9,566,060 B2 * | 2/2017 | Dougherty | A61B 17/0401 |
| 9,770,240 B2 * | 9/2017 | Dougherty | A61B 17/0469 |
| 9,782,250 B2 * | 10/2017 | Dougherty | A61F 2/0811 |
| 9,795,374 B2 * | 10/2017 | Dougherty | A61F 2/0811 |
| 9,907,548 B2 * | 3/2018 | Dougherty | A61B 17/0401 |
| 9,924,934 B2 * | 3/2018 | Housman | A61B 17/0401 |
| 9,925,036 B2 * | 3/2018 | Heaven | A61F 2/0811 |
| 2004/0193217 A1 * | 9/2004 | Lubbers | A61B 17/0401 606/232 |
| 2004/0210227 A1 * | 10/2004 | Trail | A61B 17/863 606/916 |
| 2006/0243108 A1 * | 11/2006 | Lechot | A61B 17/1624 82/52 |
| 2006/0271060 A1 * | 11/2006 | Gordon | A61B 17/0401 606/103 |
| 2007/0060922 A1 * | 3/2007 | Dreyfuss | A61B 17/0401 606/326 |
| 2008/0167660 A1 * | 7/2008 | Moreau | A61B 17/0401 606/104 |
| 2008/0275431 A1 * | 11/2008 | Stone | A61B 17/0401 606/1 |
| 2009/0082807 A1 * | 3/2009 | Miller | A61B 17/0401 606/232 |
| 2009/0312794 A1 * | 12/2009 | Nason | A61B 17/0401 606/232 |
| 2009/0326545 A1 * | 12/2009 | Schaffhausen | A61B 17/8891 606/104 |
| 2010/0004683 A1 * | 1/2010 | Hoof | A61B 17/0401 606/232 |
| 2011/0112576 A1 * | 5/2011 | Nguyen | A61B 17/0401 606/232 |
| 2011/0130760 A1 * | 6/2011 | Anderson | A61B 17/1617 606/79 |
| 2012/0053629 A1 | 3/2012 | Reiser et al. | |
| 2012/0123416 A1 * | 5/2012 | Gelfand | A61B 17/0401 606/79 |
| 2012/0165868 A1 | 6/2012 | Burkhart et al. | |
| 2013/0006276 A1 * | 1/2013 | Lantz | A61B 17/0401 606/144 |
| 2013/0150885 A1 | 6/2013 | Dreyfuss | |
| 2014/0172016 A1 * | 6/2014 | Housman | A61B 17/0401 606/232 |
| 2014/0277128 A1 * | 9/2014 | Moore | A61B 17/0642 606/232 |
| 2014/0277129 A1 * | 9/2014 | Arai | A61B 17/0401 606/232 |
| 2015/0157312 A1 | 6/2015 | Burkhart et al. | |
| 2015/0245901 A1 * | 9/2015 | Dougherty | A61F 2/0811 606/232 |
| 2016/0030159 A1 * | 2/2016 | Ticker | A61F 2/0811 606/232 |
| 2016/0310188 A1 * | 10/2016 | Marino | A61F 2/28 |

OTHER PUBLICATIONS

JP Office Action, Application No. 2020-186200, dated Oct. 14, 2021, pp. 1-6.

* cited by examiner

KNOTLESS SUTURE ANCHOR AND DEPLOYMENT DEVICE

CROSS REFERENCE TO RELATED APPLICATIONS

This application claims priority to U.S. Provisional Patent Application Ser. No. 62/268,028, which was filed on Dec. 16, 2015, the contents of which are relied upon and incorporated herein by reference in its entirety.

BACKGROUND OF THE INVENTION

1. Field of the Invention

The present invention is related to anchors for securing material to soft tissue and bone and, more particularly, to suture anchors and suture anchor deployment devices for knotlessly securing filamentary materials, and soft tissue at a surgical/repair site.

2. Description of the Related Art

Suture anchors are commonly employed during surgical procedures to secure soft tissue to bone. Such anchors are generally inserted into a pre-formed hole in the bone ("pilot hole"), so that a portion of filamentary material (e.g., suture material/sutures) extends out of the hole from the anchor and then the suture materials are passed through the tissue to be repaired. Once the tissue has been approximated to bone, the surgeon can tie one or more knots to secure the sutures. The act of tying a knot presents a number of challenges to the surgeon especially when doing them arthroscopically. See U.S. Pat. No. 8,409,252, col. 1, lines 24-41. Furthermore, in some cases, knots have been implicated as the source of post-operative pain caused by irritation from the knot stack.

Various types of suture anchors have been developed which fasten the suture in place without requiring the surgeon to tie a knot. Typically, with respect to these conventional suture anchors, the suture is captured between two opposing surfaces and held in place by friction. Some designs capture the suture between two anchor components while others utilize an interference fit between the anchor and the bone tunnel. Provided the bone quality is sufficient, the latter method provides simplicity.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

BRIEF SUMMARY OF THE INVENTION

Embodiments of the present invention recognize that there are potential problems and/or disadvantages with the conventional suture anchors and their deployment devices. For example, adjusting and maintaining the proper suture tension can be difficult and remains a lingering problem. Therefore, the need exists for a simple to use suture anchor which secures suture without the need to tie a knot and which facilitates the ability to adjust and maintain suture tension during anchor installation. Various embodiments of the present invention may be advantageous in that they may solve or reduce one or more of the potential problems and/or disadvantages discussed herein.

The present disclosure is directed to an inventive configuration, structure, and resulting function of a knotless suture anchor and the knotless suture anchor's deployment device. Various embodiments herein are directed to a cannulated implant deployment device, including, but not limited to: an elongated and cannulated driver shaft extending along a longitudinal axis including a proximal end and a distal end; a cannulated implant removably attached to the distal end of the driver shaft; a handle assembly connected to the proximal end of the driver shaft comprising a proximal handle and a knob positioned distally to the proximal handle; a cleat positioned on the driver shaft distally to the knob, wherein the cleat is structured, configured and positioned to secure a proximal end of a suture extending from a distal end of the implant, resulting in a first applied tension value of the suture extending between the proximal portion of the suture and a distal portion of the suture when the implant is placed in a pilot hole formed in a segment of bone tissue to secure the distal portion of the suture within the pilot hole; where each of the implant, proximal handle and cleat is connected to the driver shaft such that an axial rotation of the proximal handle in a first direction results in the axial rotation of the implant in the first direction and the maintenance of at least 50% of the first applied tension value when the implant is rotated in the first direction and advanced in the distal direction within the pilot hole.

According to an embodiment, the axial rotation of the proximal handle in the first direction results in the axial rotation of the implant in the first direction and the maintenance of about 100% of the first applied tension value when the implant is rotated in the first direction and advanced in the distal direction within the pilot hole.

According to an embodiment, the cleat is connected to the driver shaft such that it is configured to move in the distal direction away from the knob upon the axial rotation of the proximal handle in the first direction.

According to an embodiment, the cleat is connected to the driver shaft such that it is configured to move the same distance in the distal direction as the implant is advanced in the distal direction.

According to an embodiment, the implant contains external threading extending along at least a portion of an outside surface of the implant.

According to an embodiment, the driver shaft contains external threading extending along at least a portion of an outside surface of the driver shaft and the knob contains internal threading extending along at least a portion of an inside surface of the knob, wherein the external threading of the driver shaft mates with the internal threading of the knob forming a threaded interface, and the external threading of the driver shaft is configured to move in the distal direction in response to the axial rotation of the proximal handle in the first direction.

According to an embodiment, the pitch of the external threading of the implant is about the same as the pitch of the external threading of the driver shaft.

According to an embodiment, the knob is not fixed to and is configured to rotate around the driver shaft.

According to an embodiment, the suture is positioned through the driver shaft from the distal end of the implant through an aperture formed in the side of the driver shaft between the proximal end and the distal end of the driver shaft to the cleat on which it is secured.

According to an embodiment, the cannulated implant deployment device further comprises a suture threader positioned through the driver shaft from an aperture formed in the side of the driver shaft between the proximal end of the driver shaft and the distal end of the driver shaft through an opening in the distal end of the implant, wherein the suture threader comprises a suture catch positioned distally to the distal end of the implant sufficient to capture a portion of a suture.

According to an embodiment, the suture catch is formed as an eyelet.

According to an embodiment, the handle further comprises a locking mechanism configured to allow axial rotation of the handle in the first direction only.

According to an another aspect, a method of deploying a cannulated implant into a pilot hole formed in a segment of bone tissue includes (but is not limited to) the steps of: providing a cannulated implant deployment device including: an elongated and cannulated driver shaft extending along a longitudinal axis comprising a proximal end and a distal end; a cannulated implant removably attached to the distal end of the driver shaft; a handle assembly connected to the proximal end of the driver shaft comprising a proximal handle and a knob positioned distally to the proximal handle; and a cleat positioned on the driver shaft distally to the knob; securing a proximal end of a suture extending from a distal end of the implant to the cleat; inserting the implant into the pilot hole to secure a first distal portion of the suture within the pilot hole, and forming a first applied tension value of the suture extending between the proximal portion of the suture and the first distal portion of the suture; and rotating the proximal handle in a first direction to effectuate rotation of the implant in the first direction and the maintenance of at least 50% of the first applied tension value when the implant is rotated in the first direction and advanced in the distal direction within the pilot hole.

According to an embodiment, the step of rotating the proximal handle in the first direction results in the rotation of the implant in the first direction and the maintenance of about 100% of the first applied tension value when the implant is rotated in the first direction and advanced in the distal direction within the pilot hole.

According to an embodiment, the step of rotating the proximal handle in the first direction results in the tensioning of a second distal portion of the suture attached to a segment of soft tissue and appositioning the segment of the soft tissue to the segment of bone tissue.

According to an embodiment, the step of rotating results in the movement of the cleat in the distal direction away from the knob.

According to an embodiment, the step of rotating results in the movement of the cleat the same distance in the distal direction as the implant is advanced in the distal direction.

According to an embodiment, the method further includes the step of providing the deployment device with a suture threader positioned through the driver shaft from an aperture formed in the side of the driver shaft between the proximal end of the driver shaft and the distal end of the driver shaft through an opening in the distal end of the implant, wherein the suture threader comprises a suture catch positioned distally to the distal end of the implant.

According to an embodiment, the method further includes the steps of capturing the suture with the suture catch; and pulling the suture through the driver from the distal end of the implant through the aperture positioned between the proximal end of the driver shaft and the distal end of the driver shaft to the cleat on which it is secured prior to the step of securing.

According to a further aspect, a cannulated knotless anchor implant is provided, and can include: an elongated body extending along a longitudinal axis between a proximal end and a distal end; and a plurality of screw threads positioned about at least a portion of an exterior surface of the elongated body; where a density of the plurality of screw threads varies along the exterior surface.

Suture material or sutures, as the terms are used and described herein, include monofilament or multi-filament suture as well as any other metallic or non-metallic filamentary or wire-like material suitable for performing the function of a suture. This material can include both bioabsorbable and non-absorbable materials.

Knotless suture anchors/implants, as the terms are used and described herein, may be formed of a biocompatible and/or bioabsorbable material. These materials may be of such composition that they are reabsorbed by the body, e.g., during the healing process of the bone. Exemplary materials that are suitable for use in the inner and outer members include, but are not limited to, polyetheretherketone ("PEEK"), polylactic acid/beta-tricalcium phosphate ("PLA/Beta-TCP") composites, ultra-high molecular weight polyethylene ("UHMWPE"), as well as other metallic, non-metallic, and polymeric materials.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1A:
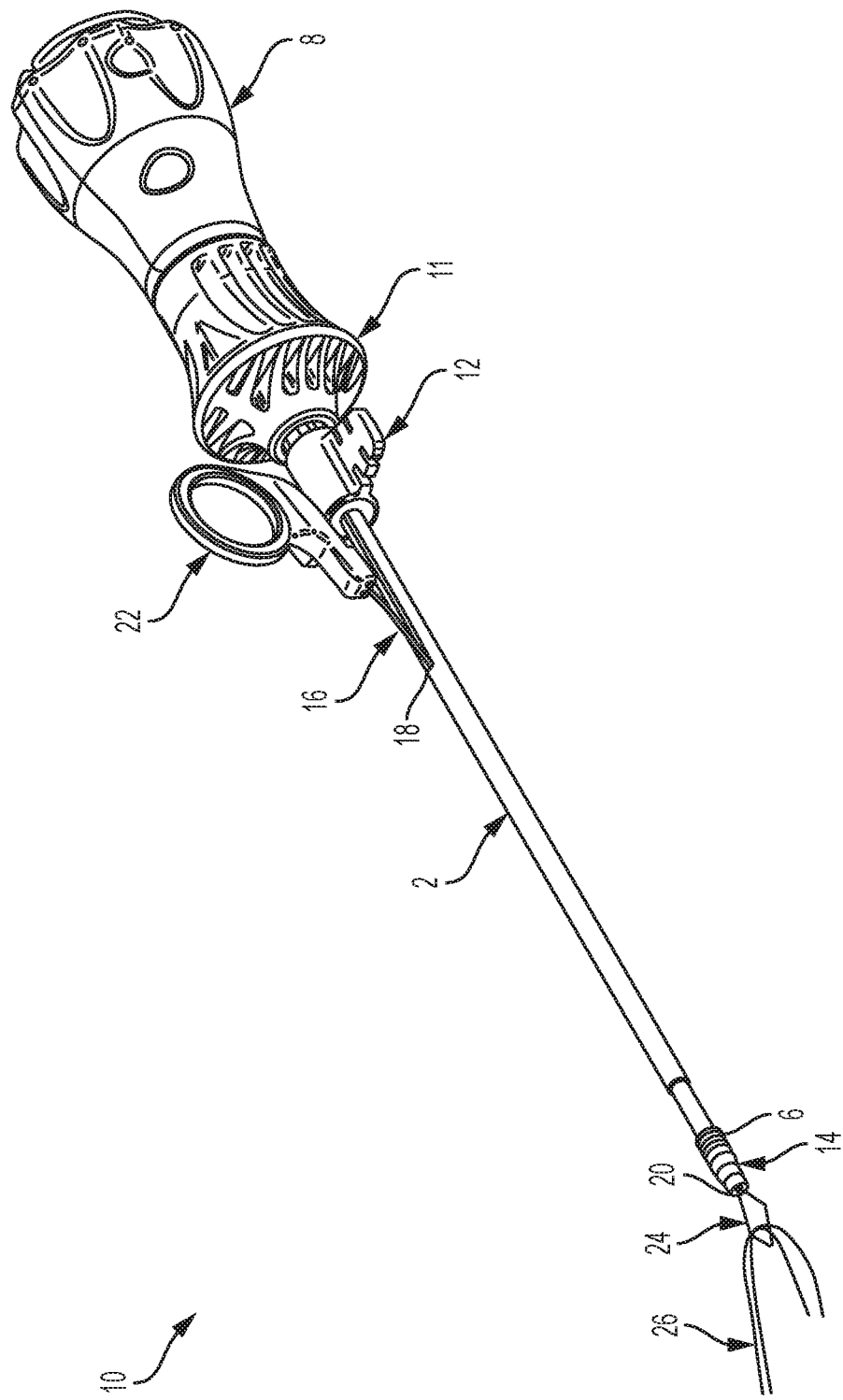
FIG. 1A is a perspective view schematic representation of a knotless anchor deployment device with a cannulated knotless anchor implant according to an embodiment.
Figure 4A:
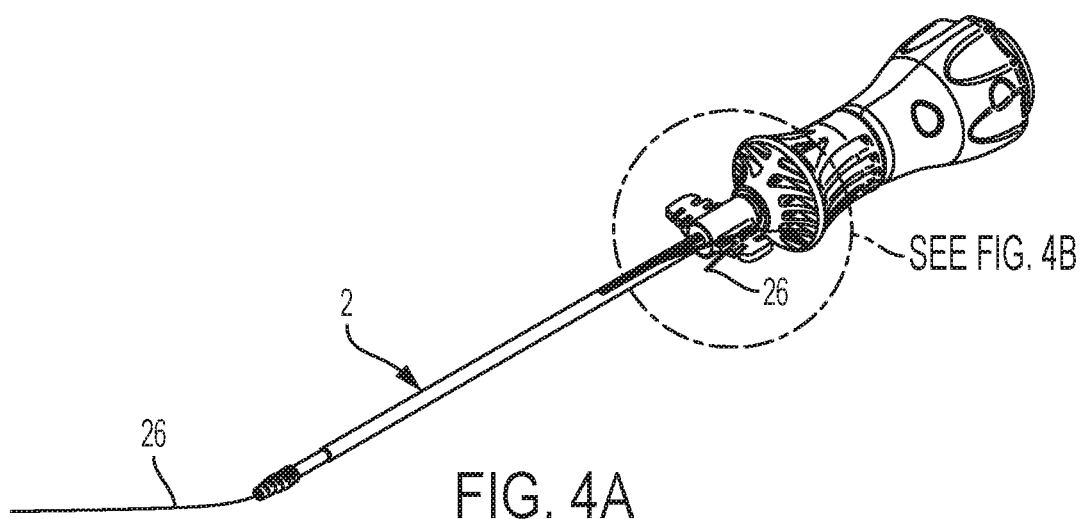
FIG. 4A is a perspective view schematic representation of a knotless anchor deployment device with a cannulated knotless anchor implant according to an embodiment.
Figure 4B:
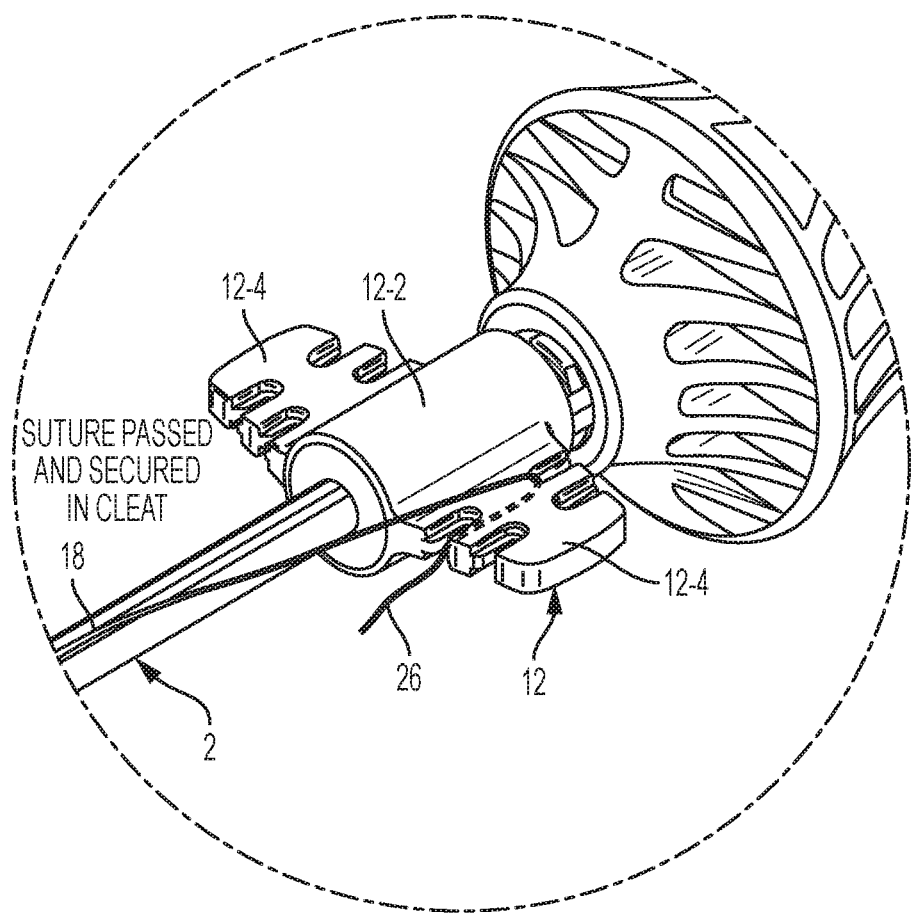
FIG. 4B is a magnified perspective view schematic representation of section "A" of the knotless anchor deployment device shown in FIG. 4A according to an embodiment.

Referring now to the drawings, wherein like reference numerals refer to like parts throughout, there is seen in FIG. 1A a knotless anchor deployment device 10 including an elongated and cannulated driver shaft 2 extending along a longitudinal axis comprising a proximal end 4 (positioned within handle 8; shown in FIG. 1D) and a distal end 6 (positioned within a cannulated knotless anchor implant 14). The cannulated knotless anchor implant 14 is removably attached to the distal end 6 of the driver shaft 2, and preferably contains external threading (but is not required to include the external threading). A handle assembly is connected to the proximal end 4 of the driver shaft 2, which includes a proximal handle 8 and a knob 11 positioned distally to the proximal handle 8. A cleat 12 is positioned on the driver shaft 2 distally to the knob 11. The cleat is formed of a central cylindrical portion 12-2 surrounding the driver shaft 2 and two cleated winged portions 12-4 (see FIGS. 4A-4B). A suture threader 16 can be positioned through an aperture 18 (which can be a hole or a channel) formed in a side of the driver shaft 2 between the proximal end of the driver shaft and the distal end of the driver shaft, and can extend through an opening 20 in the distal end of the implant 14. The threader 16 can include a finger grip 22 attached to the proximal end of the threader 16 and a suture catch 24 attached to the distal end of the threader, which can be positioned distally to the distal end of the implant 14 sufficient to capture a portion of a suture 26. The suture catch 24 as shown is shaped like an eyelet. However, any shape or structural configuration that is sufficient to capture a portion of a suture 26 is contemplated.

Figure 1B:
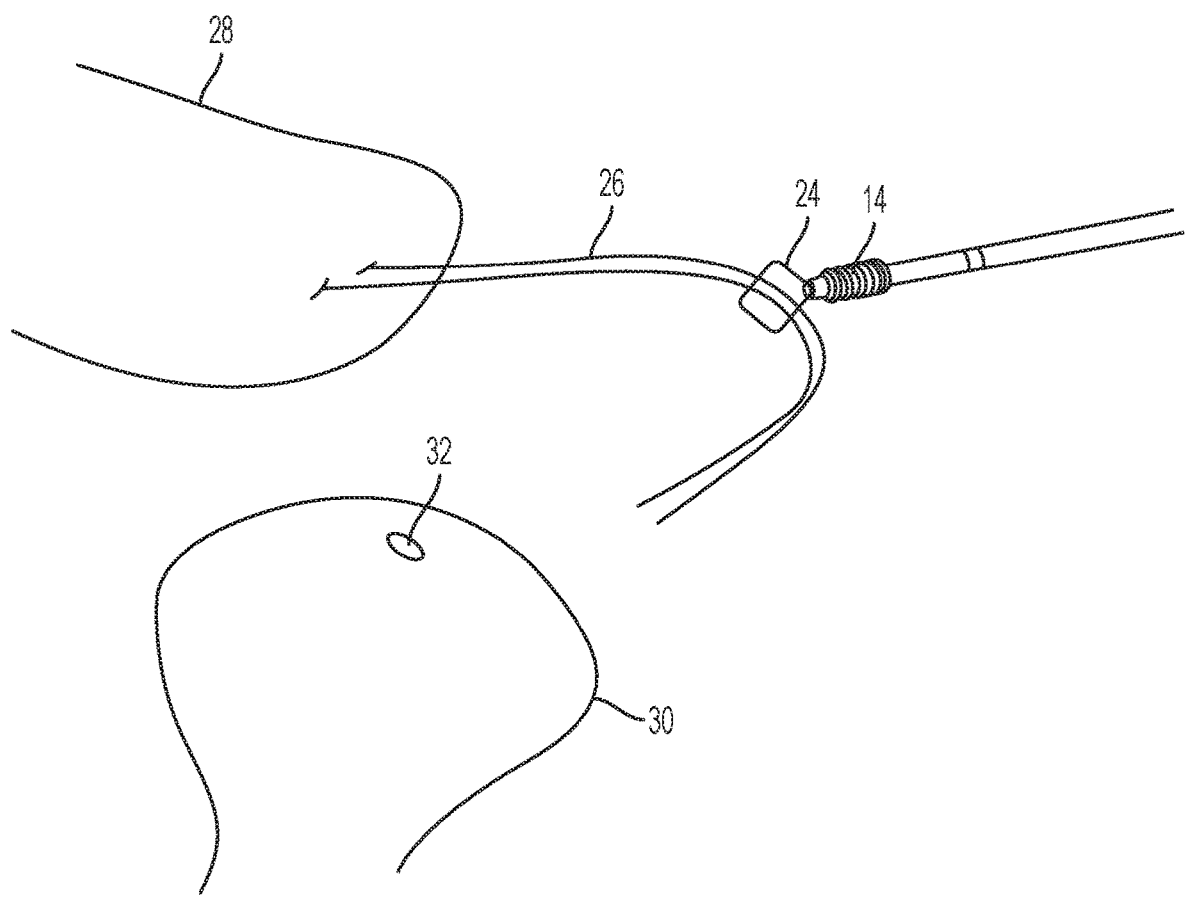
FIG. 1B is a perspective view schematic representation of a distal end of the knotless anchor deployment device with a cannulated knotless anchor implant shown in FIG. 1A according to an embodiment.
Figure 1D:
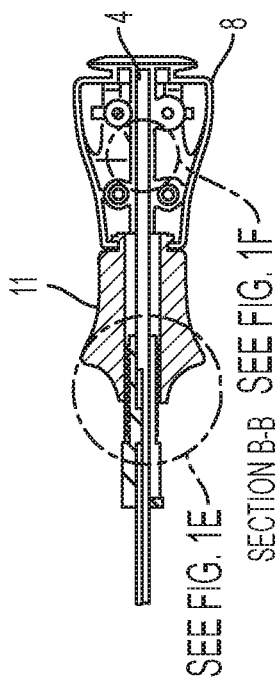
FIG. 1D is a perspective view schematic representation of section B-B of the knotless anchor deployment device shown in FIG. 1C according to an embodiment.
Figure 1F:
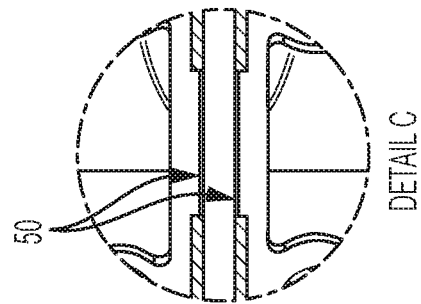
FIG. 1F is a magnified perspective view schematic representation of section "C" of the knotless anchor deployment device shown in FIG. 1D according to an embodiment.
Figure 1C:
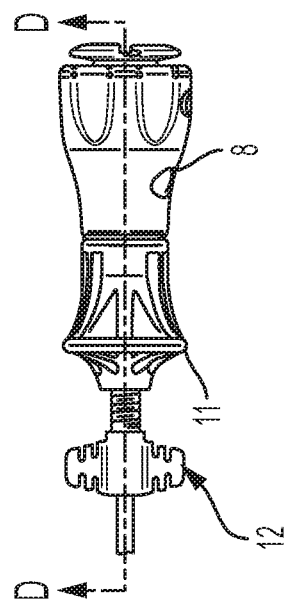
FIG. 1C is a side view schematic representation of a middle to a proximal end of the knotless anchor deployment device shown in FIG. 1A according to an embodiment.
Figure 1E:
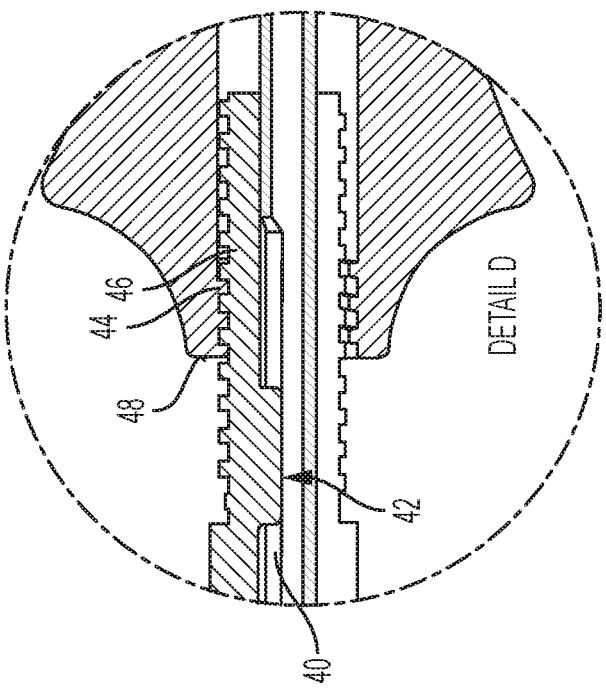
FIG. 1E is a magnified perspective view schematic representation of section "D" of the knotless anchor deployment device shown in FIG. 1D according to an embodiment.

Turning to FIG. 1C, a side view schematic representation of the middle to the proximal end of a knotless anchor deployment device shown in FIG. 1A according to an embodiment is provided. The handle 8, knob 11 and cleat 12 are shown. Referring to FIG. 1D, a perspective view schematic representation of section B-B of the knotless anchor deployment device shown in FIG. 1C according to an embodiment is provided. FIG. 1E shows a magnified perspective view schematic representation of section "D" of the knotless anchor deployment device shown in FIG. 1D according to an embodiment. Threads 46 are shown on a portion of the outer surface of the driver shaft 2, and threads 44 are shown on the inside of the knob 11 forming a threaded interface 48 with threads 46. A portion of the cleat 12 opposite the threaded interface includes a tooth 42 that engages a slot 40 formed in driver shaft 2, which connects the driver shaft 2 to the cleat 12. Referring to FIG. 1F, a magnified perspective view schematic representation of section "C" of the knotless anchor deployment device shown in FIG. 1D according to an embodiment is provided. A shaft 2/handle 8 interface 50, similar to the tooth 42 that engages a slot 40 formed in driver shaft 2, is shown which connects the driver shaft 2 to the handle 8. The tooth 42/slot 40 connection between the cleat 12 and the driver shaft 2 is configured and/or structured to allow the cleat 12 to axially rotate with the driver shaft 2. This axial movement can occur upon the axial rotation of the handle 8, which is configured and/or structured to axially rotate the driver shaft 2 based on the shaft 2/handle 8 interface 50 connection.

Figure 2:
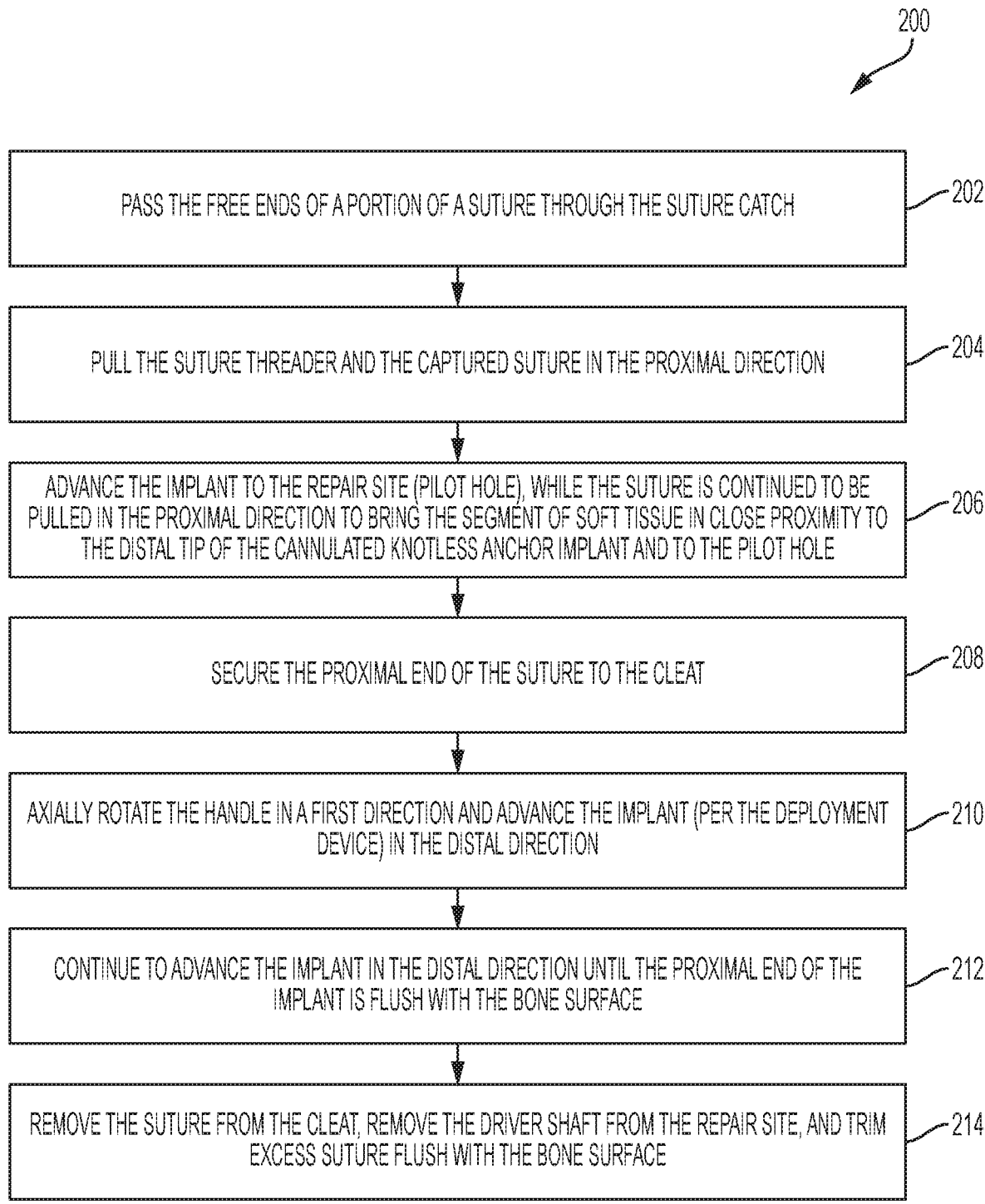
FIG. 2 is a flow chart showing a method according to an embodiment of the present invention.

In accordance with an exemplary embodiment, a method 200 of deploying the cannulated knotless anchor implant 14 with the knotless anchor deployment device 10 into a pilot hole 32 formed in a section of bone 30 is set forth in FIG. 2. The steps of the method set forth in FIG. 2 are discussed herein with reference to other Figures of this disclosure. In step 202, the free ends of a portion/length of a suture 26, which is passed through and attached on one end to a segment of soft tissue 28 (see FIG. 1B), is passed through the suture catch 24. FIG. 1B also shows a segment of bone 30 with a pilot hole 32 formed therein.

In step 204, the finger grip 22 of the suture threader 16 is pulled in the proximal direction, and the captured suture is pulled through the cannulated driver shaft 2 from the opening 20 in the distal end of the implant through the aperture 18 formed in the side of the driver shaft.

Figure 3:
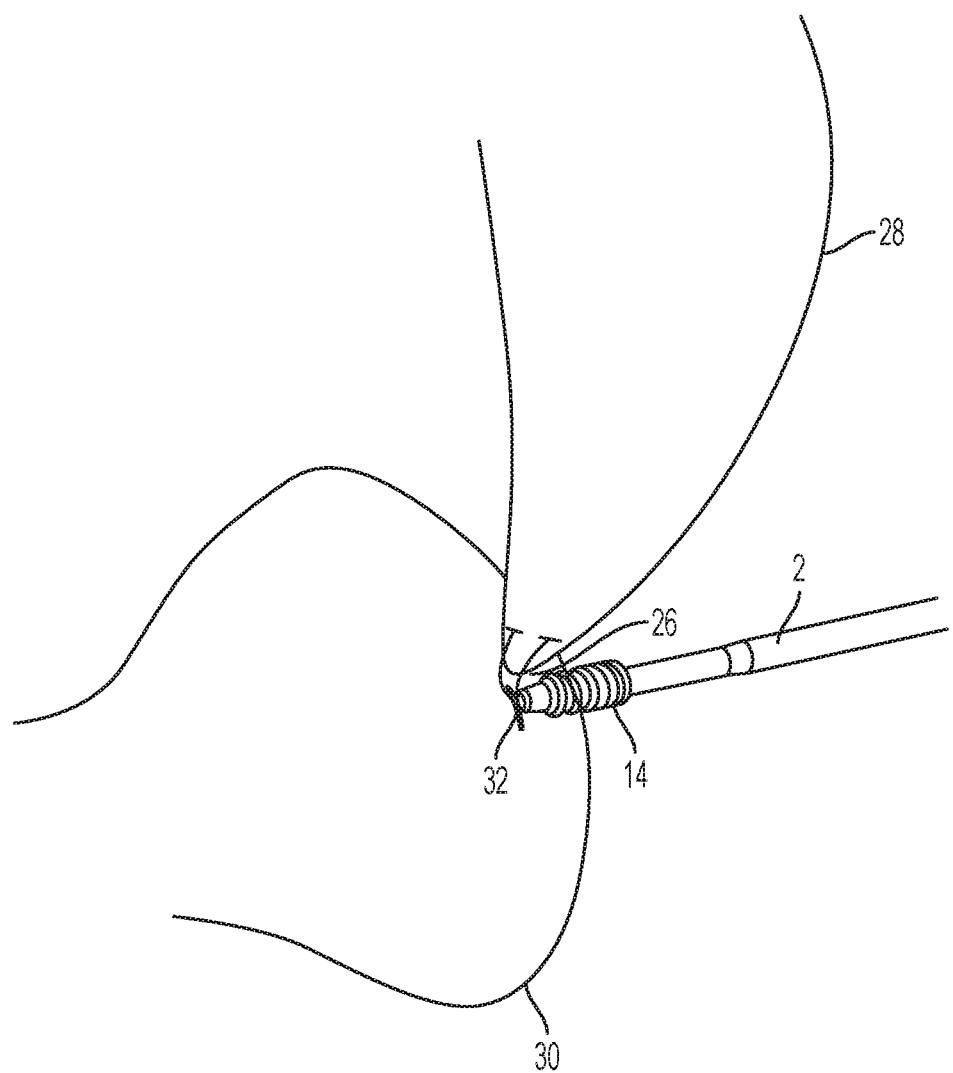
FIG. 3 is a perspective view schematic representation of a distal end of the knotless anchor deployment device with a cannulated knotless anchor implant in conjunction with a segment of soft tissue and a segment of bone according to an embodiment.

In step 206, the cannulated knotless anchor implant 14 is advanced to the repair site (pilot hole 32), while suture 26 slack is continued to be pulled through the driver shaft 2 from the opening 20 in the distal end of the implant through the aperture 18 formed in the side of the driver shaft to bring the segment of soft tissue 28 in close proximity to the distal tip of the cannulated knotless anchor implant 14 and to the pilot hole 32 (see FIG. 3).

In step 208, a proximal end of the suture 26 is secured to the cleat 12 by wrapping, for example, to either winged cleated portion of the cleat (see FIGS. 4A-4B), and the distal tip of the cannulated knotless anchor implant 14 is subsequently inserted into the pilot hole 32 pinning a distal portion of the suture between the implant 14 and the pilot hole 32. This step can result in a first applied tension value of the suture extending between the proximal portion of the suture (attached to the cleat 12) and the distal portion of the suture (within the pilot hole 32), when the implant is placed in the pilot hole 32 to secure the distal portion of the suture within the pilot hole 32. Rotation of the handle 8 can assist with the creation of the first applied tension value (which is a tension that is greater than an initial tension value, which can be generally loose suture which contains some "slack", as should be appreciated by a person of skill in the art in conjunction with a review of this disclosure), and to bring the segment of soft tissue 28 to apposition with bone. Alternatively, rotation of the knob 11 in one direction (e.g. counterclockwise) can extend the cleat 12 axially and distally away from the knob 11, and rotation of the knob in a second direction (e.g., clockwise) can bring the cleat 12 closer (move axially and proximally) to the knob 11, thereby reducing or adding to the tension value respectively. This axial movement of the cleat (and the driver shaft 2 attached to the cleat 12) can assist in fine tuning the creation and maintenance of the applied tension value without the corresponding rotation of the cleat 12 and driver shaft 2 (due to the knob's configuration with respect to the driver shaft, as it is preferably not fixed to the driver shaft 2 in the same manner as the cleat 1 and the handle 8).

Figure 5:
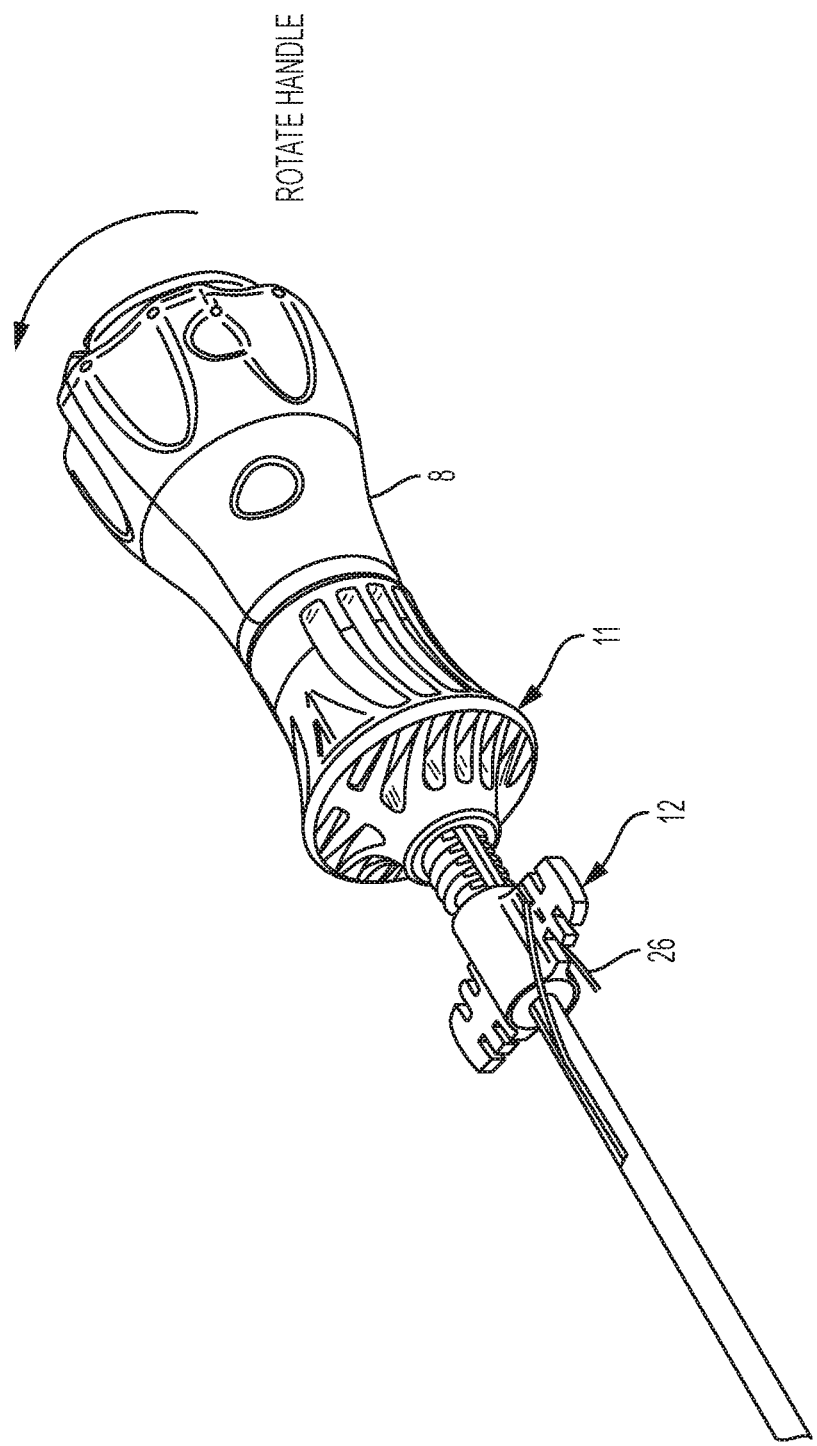
FIG. 5 is a perspective view schematic representation of a middle to a proximal end of the knotless anchor deployment device shown in FIG. 4A according to an embodiment.

In step 210, the handle 8 is axially rotated in a first direction (e.g., clockwise; see FIG. 5), and the deployment device 10 is advanced in the distal direction. The rotation of the handle 8 in the first direction results in the axial rotation of the shaft 2 and the cleat 12 in the first direction (due to the configuration etc. discussed above). This rotation also results in the axial rotation of the implant 14 in the pilot hole 32 (based on its connection to the distal end of the driver shaft 2), and assists with the advancement of the implant 14 in the distal direction into the pilot hole 32. The knob 11 is preferably held in place when the handle 8 is axially rotated, and is preferably not connected, configured, and/or structured to positively rotate in the first direction in the same way as the driver shaft 2 and the cleat 12 (i.e., it is not fixed to the driver shaft 2). If the knob 11 is not held in place, the knob 11 may axially rotate a small amount in the first direction based on a frictional engagement with other parts of the deployment device 10, but not at the same rate etc. as the handle 8, driver shaft 2, and cleat 12.

Per the axial rotation of the handle 8 in the first direction, at least 50% (and up to about 100%) of the first applied tension value is maintained when the implant 14 is rotated in the first direction and advanced in the distal direction within the pilot hole (as long each end of the suture remains secured—to the cleat and within the pilot hole, respectively). In accordance with an embodiment, a percentage of the first applied tension value is maintained based on the cleat being configured to move in the distal direction away from the knob 11 upon the axial rotation of the handle 8 in the first direction. Upon the axial rotation in the first direction, the cleat 12 is connected to the driver shaft 2 such that it is configured to move the same distance in the distal direction away from the knob 11 as the implant 14 is advanced in the distal direction within the pilot hole 14. This distal direction movement can be accomplished via the configuration of the external threading 46 on the driver shaft 2 (as described above), which forms a threaded interface 48 with the internal threading of the knob 11 and is configured to move in the distal direction in response to the axial rotation of the handle 8 in the first direction. Preferably, the pitch of the external threading of the implant 14 is about the same or exactly the same as (corresponds to) the pitch of the external threading 46 of the driver shaft 2. The cleat 12 and the implant 14 each axially rotates in the first direction and translates distally at a rate corresponding to the pitch when the handle 8 is rotated to advance the implant 14 into the pilot hole 32.

Notably, if the suture 26 were held stationary and not allowed into the pilot hole 32, the implant 14 could be damaged, over tension the segment of soft tissue 28 leading to tissue incarceration or cause it to auger out the pilot hole 32. If the suture 26 was not held (or if there was otherwise no or low tension maintained in the suture, as described) there would be a possibility of losing tension and tissue apposition to bone resulting in a bad repair.

Figure 6:
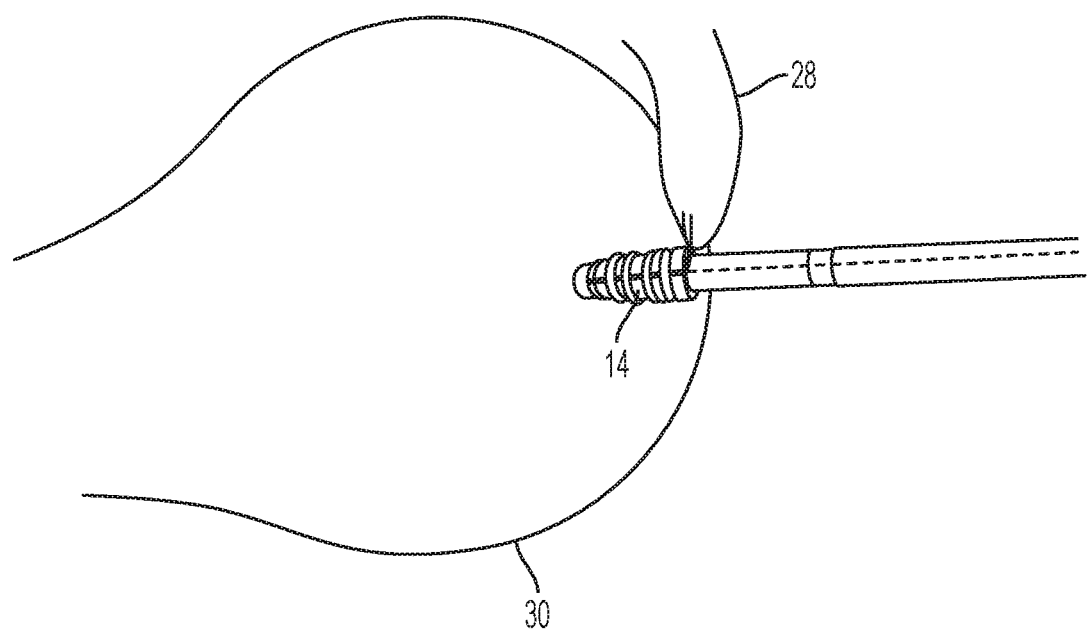
FIG. 6 is a perspective view schematic representation of a distal end of the knotless anchor deployment device with a cannulated knotless anchor implant in conjunction with a segment of soft tissue and a segment of bone according to an embodiment.

In step 212, the implant 14 is advanced until its proximal end is flush with the bone 30 surface (see FIG. 6).

Figure 7:
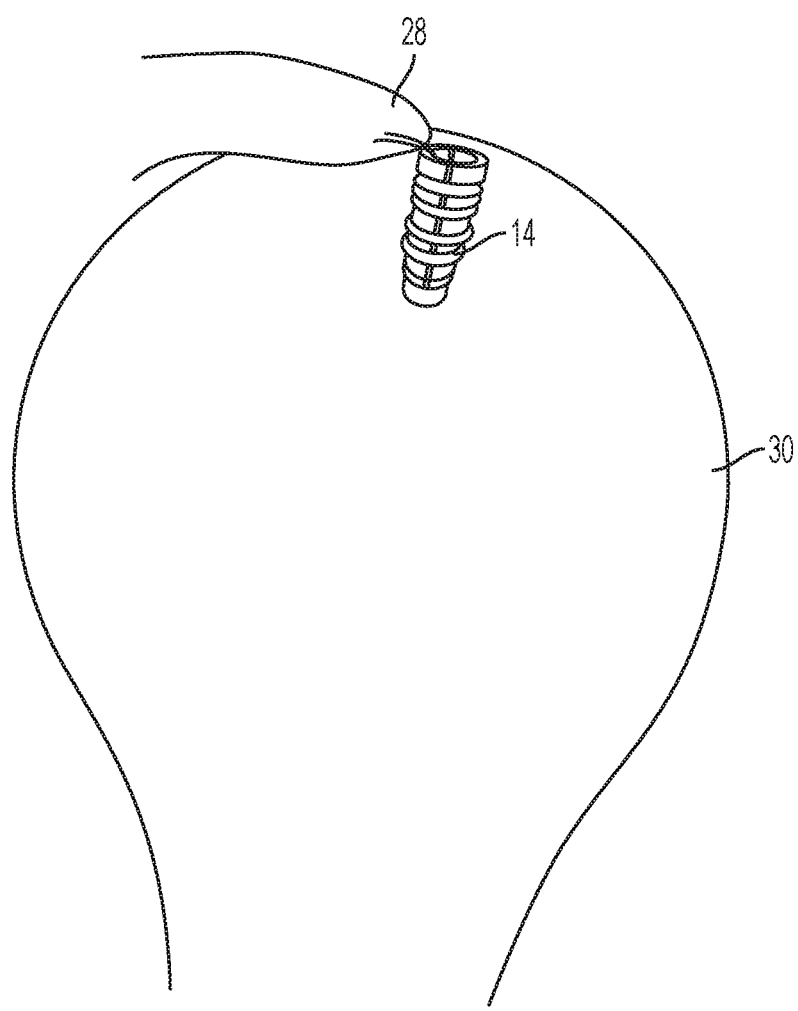
FIG. 7 is a perspective view schematic representation of the segment of soft tissue secured to the segment of bone with the implant and suture according to an embodiment.
Figure 8:
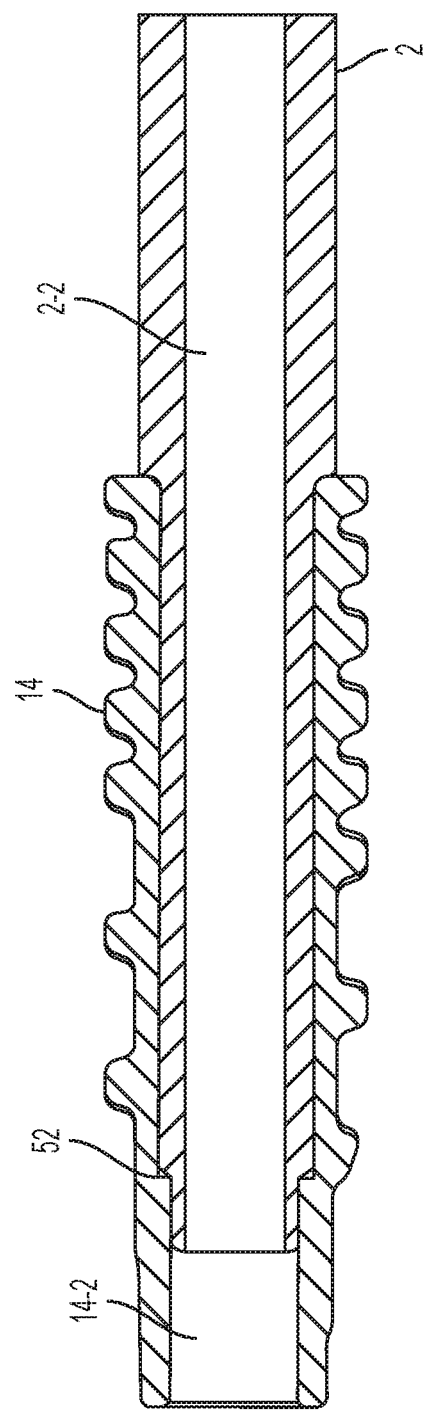
FIG. 8 is a longitudinal sectional view schematic representation of the implant attached to the distal end of the driver shaft of the deployment device according to an embodiment.

In step 214, the suture can be removed from the cleat 12, the implant 14 can be deployed, and the driver shaft 2 can be removed from the repair site (see FIG. 7). The driver shaft 2 is pulled free from the implant 14 positioned within the pilot hole 32, leaving the implant 1 within the pilot hole 32. As shown in FIG. 8, the implant 14 is attached to the distal end 6 of the driver shaft 2 via a friction fit. The lumen 2-2 of the driver shaft 2 within the lumen of the implant 14 is shown, and the lumen 14-2 of the implant without containing a portion of the driver shaft is also shown. The distal tip of the driver shaft 2 contains a cylindrical portion which is sized to create a slight interference with the cannulation of the implant 14. For example, a stepped interface 52 between the lumen of the distal portion of the distal end of the driver shaft 2 and the lumen of the implant 14 is provided. This stepped interface 52 or additional stepped interfaces can exist in different positions between the lumen of the driver shaft 2 and the implant 14. Another purpose of the stepped interface is to help prevent the driver shaft 2 from extending distally beyond the implant 14 during deployment. The force of the friction fit is preferably less than the force of the fit between the implant 14 and the pilot hole 32, allowing the deployment device to be easily removed from the implant 14 and the pilot hole 32 after the implant 14 is deployed within the pilot hole 32. The excess suture can be trimmed flush with the bone surface completing the repair.

Figure 9:
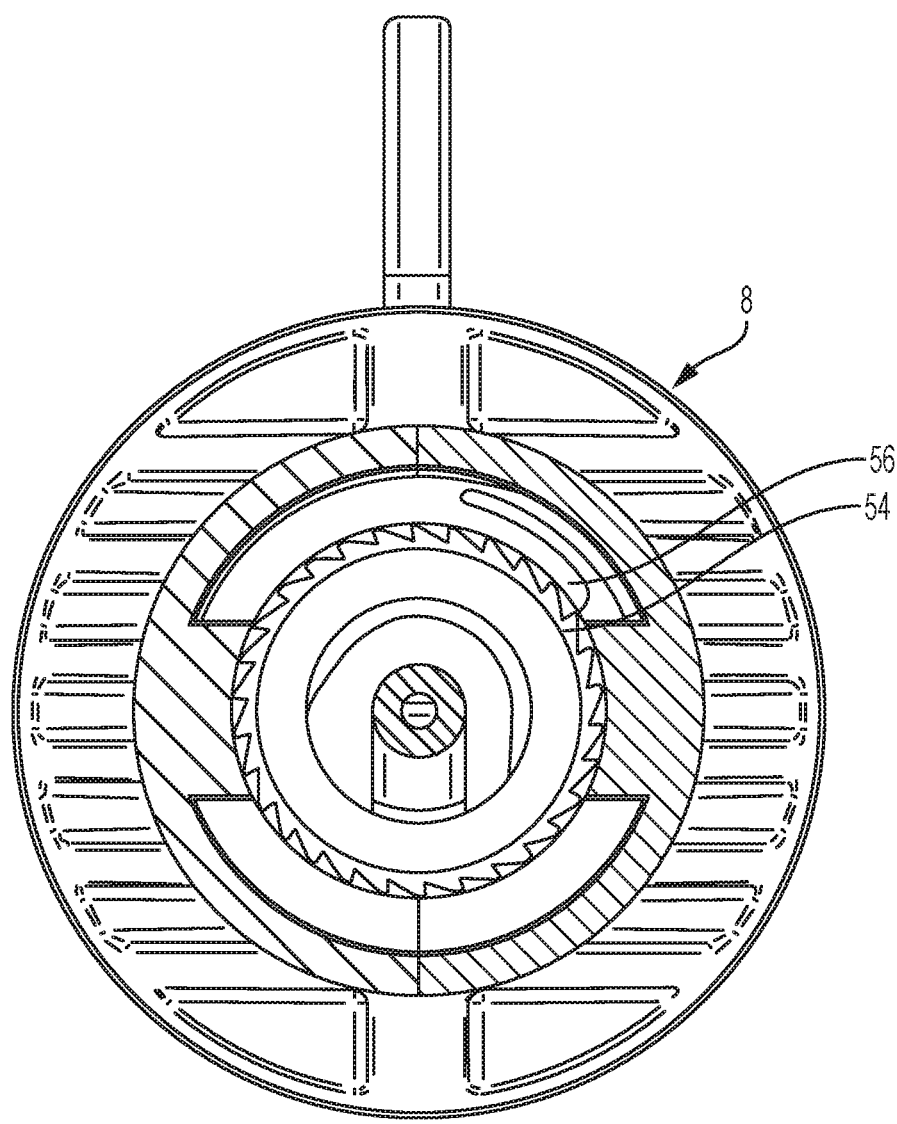
FIG. 9 is a sectional view from the proximal end of a handle showing a ratcheting or locking mechanism within the handle according to an embodiment.

In some embodiments (see FIG. 9), the handle 8 can further include a ratcheting or locking mechanism including a round gear 54 with teeth and a biased, spring loaded/cantilevered finger 56 configured to allow axial rotation of the handle 8 (and thus, the driver shaft 2, the cleat 12, and the implant 14) in the first direction only. As a user rotates the handle in the first (clockwise) direction, the distal end of the finger 56 moves from fitting between one set of teeth to a second set of teeth on the round gear 54—where the round gear 54 is locked from moving in the opposite (counterclockwise) direction. This configuration preferably ensures that the tension is maintained during manipulation and placement of the implant 14 into the pilot hole 32. The ratcheting or locking mechanism can include any type of mechanism which does not allow axial rotation in one direction, as should be appreciated by one of skill in the art in conjunction with a review of this disclosure.

Figure 10:
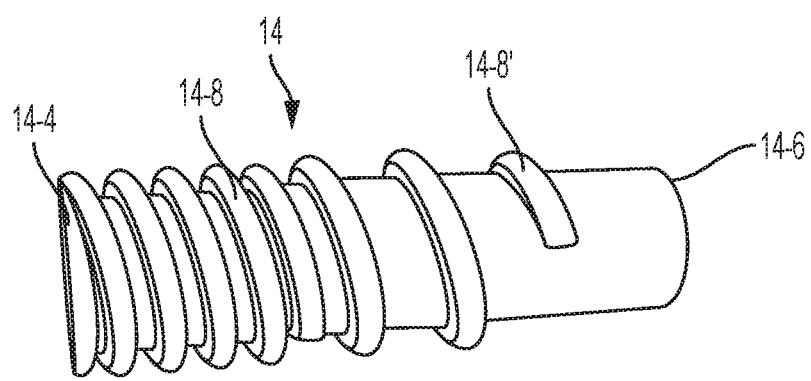
FIG. 10 is a perspective view of a cannulated knotless anchor implant according to an embodiment.

Turning to FIG. 10, a perspective view of a cannulated knotless anchor implant 14 in accordance with an embodiment is shown. The cannulated knotless anchor implant 14 can include an elongated body extending along a longitudinal axis between a proximal end 14-4 and a distal end 14-6. The cannulated knotless anchor implant 14 can also include a screw thread 14-8 positioned about the exterior surface of the knotless anchor implant 14. The screw thread 14-8 can be continuous or non-continuous, where each revolution or apparent revolution around the elongated body can be deemed a separate screw thread creating a plurality of screw threads (even though screw thread 14-8 may be continuous). The screw thread 14-8 can extend (1) from the most proximal portion of the proximal end to the most distal portion of the distal end, (2) from the most proximal portion of the proximal end to a position prior to the most distal portion of the distal end, (3) from a position between the most proximal portion of the proximal end and the most distal portion of the distal end to another position between the most proximal portion of the proximal end and the most distal portion of the distal end, or (4) any combination of the foregoing positions (or any other position on the exterior surface of the exterior portion of the cannulated knotless anchor implant 14). The screw threads 14-8 can be positioned all the way around the exterior surface of the cannulated knotless anchor implant 14, partially around the exterior surface of the cannulated knotless anchor implant 14 (e.g., ¼, ½, ¾, of the way around), or can include a combination thereof. Additionally, a density of a number of screw threads can vary along the exterior surface of the cannulated knotless anchor implant 14. For example, the density of the number of screw threads 14-8 positioned about the exterior surface of the cannulated knotless anchor implant 14 can be greater between the proximal end 14-4 and about half way towards the distal end 14-6 as compared to the density of the number of screw threads 14-8' positioned about the exterior surface of the knotless anchor implant 14 between about half way towards the distal end 14-6 and the distal end 14-6. Further, the lumen 14-2 of the elongated body can comprise more than one diameter, e.g., the proximal end 14-4 can include a larger diameter than the distal end 14-6. This difference in diameter size can be based on differences in shape between sections of the elongated body (e.g., conical vs. different sized cylindrical sections), or the narrowing or enlargement of the size of the lumen at any given point along the longitudinal axis based on changes in the thickness of the interior wall sections of the elongated body.

Figure 11:
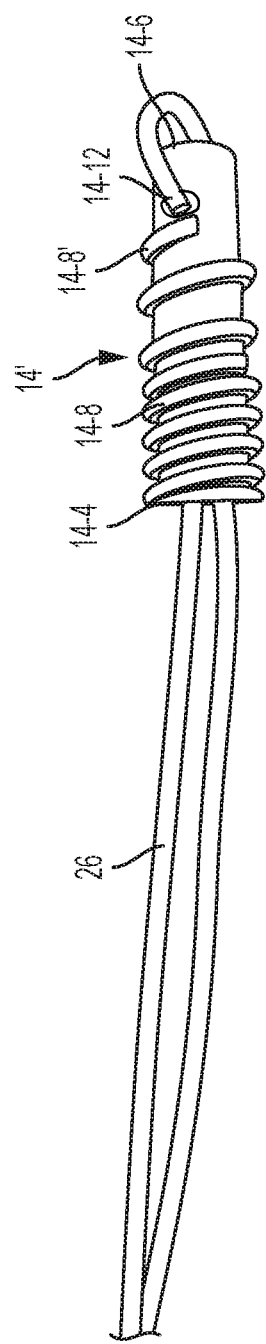
FIG. 11 is a perspective view of a cannulated knotless anchor implant according to an alternative embodiment.

Turning to FIG. 11, a perspective view of a cannulated knotless anchor implant 14' in accordance with an alternative embodiment is shown. The majority of the features of cannulated knotless anchor implant 14' are similar to the cannulated knotless anchor implant 14. However, cannulated knotless anchor implant 14' also includes at least one laterally positioned hole 14-12, which is substantially transverse to the lumen 14-2. A suture 26 is shown positioned through the hole 14-12. The laterally positioned hole or holes 14-12 can be positioned through one portion of the exterior surface or through two portions of the exterior surface, which can be, but do not need to be, directly across from each other, and can be next to each other.

While embodiments of the present invention has been particularly shown and described with reference to certain exemplary embodiments, it will be understood by one skilled in the art that various changes in detail may be effected therein without departing from the spirit and scope of the invention as defined by claims that can be supported by the written description and drawings. Further, where exemplary embodiments are described with reference to a certain number of elements it will be understood that the exemplary embodiments can be practiced utilizing either less than or more than the certain number of elements.

What is claimed is:

1. A cannulated implant deployment device, comprising:
an elongated and cannulated driver shaft extending along a longitudinal axis comprising a proximal end and a distal end;
a cannulated implant comprising a proximal end and a distal end and being removably attached to the distal end of the driver shaft, wherein the distal end of the driver shaft is the most distal tubular portion of the deployment device, and wherein the interior portion of the implant is configured to prevent the distal end of the driver shaft from extending beyond the distal end of the implant;
a handle assembly connected to the proximal end of the driver shaft comprising a proximal handle and a knob positioned distally to the proximal handle;
a cleat positioned on the driver shaft distally to the knob, wherein the cleat is structured, configured and positioned to secure a proximal end of a suture extending from a distal end of the implant, resulting in a first applied tension value of the suture extending between the proximal portion of the suture and a distal portion of the suture when the implant is placed in a pilot hole formed in a segment of bone tissue to secure the distal portion of the suture within the pilot hole;
wherein each of the implant, proximal handle and cleat is connected to the driver shaft such that the proximal handle is configured to be axially rotated in a first direction, and the implant is configured to axially rotate in the first direction upon the axial rotation of the proximal handle and to advance in the distal direction within the pilot hole, and at least 50% of the first applied tension value is capable of being maintained when the implant is rotated in the first direction and advanced in the distal direction within the pilot hole.

2. The deployment device of claim 1, wherein the implant is configured to axially rotate in the first direction upon the axial rotation of the proximal handle and to advance in the distal direction within the pilot hole, and about 100% of the first applied tension value is capable of being maintained when the implant is rotated in the first direction and advanced in the distal direction within the pilot hole.

3. The deployment device of claim 1, wherein the cleat is connected to the driver shaft such that it is configured to move in the distal direction away from the knob upon the axial rotation of the proximal handle in the first direction.

4. The deployment device of claim 3, wherein the cleat is connected to the driver shaft such that it is configured to move the same distance in the distal direction as the implant is advanced in the distal direction.

5. The deployment device of claim 4, wherein the implant contains external threading extending along at least a portion of an outside surface of the implant.

6. The deployment device of claim 5, wherein the driver shaft contains external threading extending along at least a portion of an outside surface of the driver shaft and the knob contains internal threading extending along at least a portion of an inside surface of the knob, wherein the external threading of the driver shaft mates with the internal threading of the knob forming a threaded interface, and the external threading of the driver shaft is configured to move in the distal direction in response to the axial rotation of the proximal handle in the first direction.

7. The deployment device of claim 6, wherein the pitch of the external threading of the implant is about the same as the pitch of the external threading of the driver shaft.

8. The deployment device of claim 1, wherein the knob is not fixed to and is configured to rotate around the driver shaft.

9. The deployment device of claim 1, wherein the suture is positioned through the driver shaft from the distal end of the implant through an aperture formed in the side of the driver shaft between the proximal end and the distal end of the driver shaft to the cleat on which it is secured.

10. The deployment device of claim 9, further comprising a suture threader positioned through the driver shaft from an aperture formed in the side of the driver shaft between the proximal end of the driver shaft and the distal end of the driver shaft through an opening in the distal end of the implant, wherein the suture threader comprises a suture catch positioned distally to the distal end of the implant sufficient to capture a portion of a suture.

11. The deployment device of claim 10, wherein the suture catch is formed as an eyelet.

12. The deployment device of claim 1, wherein the handle further comprises a locking mechanism configured to allow axial rotation of the handle in the first direction only.

13. A method of deploying a cannulated implant into a pilot hole formed in a segment of bone tissue, the method comprising the steps of:
   providing a cannulated implant deployment device comprising:
      an elongated and cannulated driver shaft extending along a longitudinal axis comprising a proximal end and a distal end;
      a cannulated implant comprising a proximal end and a distal end and being removably attached to the distal end of the driver shaft, wherein the distal end of the driver shaft is the most distal tubular portion of the deployment device, and wherein the interior portion of the implant is configured to prevent the distal end of the driver shaft from extending beyond the distal end of the implant;
      a handle assembly connected to the proximal end of the driver shaft comprising a proximal handle and a knob positioned distally to the proximal handle; and
      a cleat positioned on the driver shaft distally to the knob;
   securing a proximal end of a suture extending from a distal end of the implant to the cleat;
   inserting the implant into the pilot hole to secure a first distal portion of the suture within the pilot hole, and forming a first applied tension value of the suture extending between the proximal portion of the suture and the first distal portion of the suture; and
   rotating the proximal handle in a first direction to effectuate rotation of the implant in the first direction and the maintenance of at least 50% of the first applied tension value when the implant is rotated in the first direction and advanced in the distal direction within the pilot hole.

14. The method of claim 13, wherein the step of rotating the proximal handle in the first direction results in the rotation of the implant in the first direction and the maintenance of about 100% of the first applied tension value when the implant is rotated in the first direction and advanced in the distal direction within the pilot hole.

15. The method of claim 13, wherein the step of rotating the proximal handle in the first direction results in the tensioning of a second distal portion of the suture attached to a segment of soft tissue and appositioning the segment of the soft tissue to the segment of bone tissue.

16. The method of claim 13, wherein the step of rotating results in the movement of the cleat in the distal direction away from the knob.

17. The method of claim 16, wherein the step of rotating results in the movement of the cleat the same distance in the distal direction as the implant is advanced in the distal direction.

18. The method of claim 13, further comprising the step of providing the deployment device with a suture threader positioned through the driver shaft from an aperture formed in the side of the driver shaft between the proximal end of the driver shaft and the distal end of the driver shaft through an opening in the distal end of the implant, wherein the suture threader comprises a suture catch positioned distally to the distal end of the implant.

19. The method of claim 18, further comprising the steps of:
   capturing the suture with the suture catch; and
   pulling the suture through the driver from the distal end of the implant through the aperture positioned between the proximal end of the driver shaft and the distal end of the driver shaft to the cleat on which it is secured prior to the step of securing.

* * * * *